United States Patent
Hou et al.

(10) Patent No.: US 11,129,914 B1
(45) Date of Patent: Sep. 28, 2021

(54) ETHYLENE OXIDE ADSORPTION TOWER AND RECOVERY SYSTEM, AND METHOD FOR RECOVERING ETHYLENE OXIDE

(71) Applicants: Chio Kang Medical, Inc., Palo Alto, CA (US); Qiaokang Biotech (Guangdong) Co., LTD., Guangzhou (CN)

(72) Inventors: Dongxin Hou, Guangzhou (CN); Jianlong Xue, Guangzhou (CN); Shengwei Hu, Guangzhou (CN); Weiguo Wang, Guangzhou (CN); Yecheng He, Guangzhou (CN); Qinghua Xiao, Guangzhou (CN); Ziping Zhu, Guangzhou (CN); Lixiong Feng, Palo Alto, CA (US)

(73) Assignees: Chio Kang Medical, Inc., Palo Alto, CA (US); Qiaokang Biotech (Guangdong) Co., LTD., Guangzhou (CN)

( * ) Notice: Subject to any disclaimer, the term of this patent is extended or adjusted under 35 U.S.C. 154(b) by 0 days.

(21) Appl. No.: 17/002,523

(22) Filed: Aug. 25, 2020

Related U.S. Application Data

(63) Continuation of application No. PCT/CN2020/100125, filed on Jul. 3, 2020.

(30) Foreign Application Priority Data

Mar. 19, 2020 (CN) .......................... 202010194449.1
Mar. 19, 2020 (CN) .......................... 202010194457.6
(Continued)

(51) Int. Cl.
*A61L 2/20* (2006.01)
*B01D 53/04* (2006.01)
*A61L 2/26* (2006.01)

(52) U.S. Cl.
CPC .................. *A61L 2/206* (2013.01); *A61L 2/26* (2013.01); *B01D 53/0438* (2013.01);
(Continued)

(58) Field of Classification Search
CPC ....... A61L 2/206; A61L 2/26; B01D 53/0438; B01D 53/0446; B01D 53/0454;
(Continued)

(56) References Cited

U.S. PATENT DOCUMENTS 1,954,056 A 4/1934 Miller
2,586,670 A 2/1952 Lambertsen
(Continued)

FOREIGN PATENT DOCUMENTS

CN 1223166 A 7/1999
CN 101224381 A 7/2008
(Continued)

OTHER PUBLICATIONS

CN210088451U_ENG (Espacenet machine translation of Zheng) (Year: 2020).*
(Continued)

*Primary Examiner* — Jonathan Miller
*Assistant Examiner* — Gabriel E Gitman
(74) *Attorney, Agent, or Firm* — Adsero IP

(57) ABSTRACT

An ethylene oxide adsorption recovery system includes a tower body defining a gas channel extending longitudinally therein. A sidewall of the tower body further comprises a plurality of mounting holes disposed longitudinally along the side wall and in communication with the gas channel. A bottom portion of the tower body includes a first pipe in communication with the gas channel, and a top portion of the tower body includes a second pipe in communication with the gas channel. A plurality of adsorption panels is coupled to the tower body through corresponding respective
(Continued)

mounting holes of the plurality of mounting holes, each of the plurality of adsorption panels extends into the gas channel. A sealing door is movably coupled to the sidewall of the tower body and configured to selectively fix each of the plurality of adsorption panels to a respective mounting hole of the plurality of mounting hole.

21 Claims, 9 Drawing Sheets

(30) Foreign Application Priority Data

Mar. 19, 2020 (CN) .......................... 202020348760.2
Mar. 19, 2020 (CN) .......................... 202020348776.3

(52) U.S. Cl.
CPC ..... *B01D 53/0446* (2013.01); *B01D 53/0454* (2013.01); *B01D 2257/708* (2013.01); *B01D 2258/02* (2013.01); *B01D 2259/40086* (2013.01); *B01D 2259/40092* (2013.01); *B01D 2259/41* (2013.01); *B01D 2259/45* (2013.01)

(58) Field of Classification Search
CPC ........... B01D 2259/40086; B01D 2259/40092; B01D 2259/41; B01D 2259/45; B01D 2257/708; B01D 2258/02
See application file for complete search history.

(56) References Cited

U.S. PATENT DOCUMENTS

| | | | |
|---|---|---|---|
| 2,817,689 A | | 12/1957 | White |
| 3,572,391 A | | 3/1971 | Hirsch et al. |
| 3,598,543 A | | 8/1971 | Crosby et al. |
| 3,844,739 A | | 10/1974 | Alfrey, Jr. |
| 3,961,920 A | * | 6/1976 | Gilbert ............... B01D 53/0407 96/129 |
| 3,997,633 A | | 12/1976 | Leva et al. |
| 4,112,054 A | | 9/1978 | Feingold et al. |
| 4,119,539 A | | 10/1978 | Ettel et al. |
| 4,134,425 A | | 1/1979 | Gussefeld et al. |
| 4,301,113 A | | 11/1981 | Alguire et al. |
| 4,517,167 A | | 5/1985 | Popescu et al. |
| 4,549,363 A | | 10/1985 | Buonicore |
| 4,555,251 A | | 11/1985 | Jonsson |
| 4,831,196 A | | 5/1989 | Buonicore et al. |
| 5,084,075 A | | 1/1992 | Sircar |
| 5,204,075 A | * | 4/1993 | Jain ...................... F25J 3/04739 423/219 |
| 5,270,000 A | | 12/1993 | Goldner et al. |
| 5,283,035 A | * | 2/1994 | Karthaus ................. A61L 2/206 422/31 |
| 5,290,345 A | * | 3/1994 | Osendorf ........... B01D 53/0446 55/385.2 |
| 5,511,409 A | * | 4/1996 | Knaebel ............. G01N 33/0011 73/28.04 |
| 5,522,808 A | | 6/1996 | Skalla |
| 5,607,652 A | | 3/1997 | Hellmuth et al. |
| 5,641,455 A | | 6/1997 | Rosenlund et al. |
| 5,702,669 A | | 12/1997 | Green et al. |
| 5,741,470 A | | 4/1998 | Wenzler |
| 5,755,857 A | * | 5/1998 | Acharya ............ B01D 53/0462 96/122 |
| 5,779,773 A | | 7/1998 | Cam et al. |
| 5,964,927 A | * | 10/1999 | Graham ............ B01D 53/0446 96/121 |
| 6,156,101 A | | 12/2000 | Naheiri |
| 6,684,648 B2 | | 2/2004 | Faqih |
| 6,743,402 B2 | | 6/2004 | Shimakawa |
| 7,316,733 B1 | | 1/2008 | Hedrick |
| 7,625,535 B2 | | 12/2009 | Yamaguchi |
| 8,110,156 B2 | | 2/2012 | Ricciardi et al. |
| 8,431,085 B2 | | 4/2013 | Froderberg et al. |
| 9,616,143 B2 | | 4/2017 | Snyder et al. |
| 10,987,443 B1 | | 4/2021 | Hu et al. |
| 2002/0046569 A1 | | 4/2002 | Faqih |
| 2002/0197194 A1 | | 12/2002 | Machado et al. |
| 2005/0145108 A1 | | 7/2005 | Rubin |
| 2006/0236860 A1 | | 10/2006 | Sumida et al. |
| 2006/0249027 A1 | * | 11/2006 | Adolphsen ............... F24F 3/161 96/134 |
| 2007/0209383 A1 | | 9/2007 | Hutton |
| 2008/0078289 A1 | * | 4/2008 | Sergi ...................... B01D 46/10 95/25 |
| 2008/0080999 A1 | * | 4/2008 | Bondar ................... A61L 2/206 422/31 |
| 2008/0289591 A1 | | 11/2008 | Tessier et al. |
| 2010/0196194 A1 | * | 8/2010 | Voeten ...................... A61L 2/24 422/3 |
| 2011/0265644 A1 | * | 11/2011 | Swami ................ C01B 13/0251 95/22 |
| 2011/0283885 A1 | | 11/2011 | Thiele |
| 2012/0031268 A1 | | 2/2012 | Yaghi et al. |
| 2012/0298207 A1 | | 11/2012 | Woelk et al. |
| 2014/0119989 A1 | | 5/2014 | Hayashi et al. |
| 2014/0251130 A1 | | 9/2014 | Sprinkle et al. |
| 2014/0290162 A1 | | 10/2014 | Tanimoto |
| 2016/0010883 A1 | | 1/2016 | Jornitz et al. |
| 2017/0056813 A1 | | 3/2017 | McMahon et al. |
| 2019/0076776 A1 | | 3/2019 | Mahecha-Botero et al. |
| 2019/0151791 A1 | | 5/2019 | Awadh et al. |
| 2019/0175971 A1 | | 6/2019 | Moore et al. |
| 2020/0148655 A1 | | 5/2020 | Duff et al. |

FOREIGN PATENT DOCUMENTS

| | | | | |
|---|---|---|---|---|
| CN | 101549241 A | | 10/2009 | |
| CN | 101773762 A | | 7/2010 | |
| CN | 201632182 U | | 11/2010 | |
| CN | 102173384 A | | 9/2011 | |
| CN | 102219642 A | | 10/2011 | |
| CN | 102921570 A | | 2/2013 | |
| CN | 202802975 U | | 3/2013 | |
| CN | 202933710 U | | 5/2013 | |
| CN | 103394278 A | | 11/2013 | |
| CN | 103657383 A | | 3/2014 | |
| CN | 103706233 A | | 4/2014 | |
| CN | 203507806 U | | 4/2014 | |
| CN | 203564952 U | | 4/2014 | |
| CN | 103800926 A | | 5/2014 | |
| CN | 203749877 U | | 8/2014 | |
| CN | 203750388 U | | 8/2014 | |
| CN | 203750389 U | | 8/2014 | |
| CN | 104014227 A | | 9/2014 | |
| CN | 104275085 A | | 1/2015 | |
| CN | 204261680 U | | 4/2015 | |
| CN | 204447972 U | | 7/2015 | |
| CN | 104815535 A | | 8/2015 | |
| CN | 105132060 A | | 12/2015 | |
| CN | 105327665 A | | 2/2016 | |
| CN | 105664822 A | | 2/2016 | |
| CN | 205300112 U | | 6/2016 | |
| CN | 106475021 A | | 3/2017 | |
| CN | 106582126 A | * | 4/2017 | ......... B01D 46/0006 |
| CN | 206535551 U | | 10/2017 | |
| CN | 206853397 U | | 1/2018 | |
| CN | 107677016 A | | 2/2018 | |
| CN | 207169397 U | | 4/2018 | |
| CN | 207187436 U | | 4/2018 | |
| CN | 207745676 U | | 8/2018 | |
| CN | 207913454 U | | 9/2018 | |
| CN | 108607511 A | | 10/2018 | |
| CN | 208218734 U | | 12/2018 | |
| CN | 109382064 A | | 2/2019 | |
| CN | 208448985 U | | 2/2019 | |
| CN | 208893903 U | | 5/2019 | |
| CN | 110145747 A | | 8/2019 | |
| CN | 110302634 A | | 10/2019 | |
| CN | 110404485 A | | 11/2019 | |

(56) References Cited

FOREIGN PATENT DOCUMENTS

| | | | | |
|---|---|---|---|---|
| CN | 209662917 U | | 11/2019 | |
| CN | 110833754 A | | 2/2020 | |
| CN | 210021633 U | | 2/2020 | |
| CN | 210088451 U | * | 2/2020 | ............ B01D 53/02 |
| DE | 4236622 C1 | | 3/1994 | |
| EP | 0130319 A2 | * | 1/1985 | ............ A61L 2/206 |
| EP | 0350677 A1 | * | 1/1990 | ......... B01D 53/0438 |
| EP | 1302478 A1 | | 4/2003 | |
| EP | 2883598 A1 | | 6/2015 | |
| GB | 1472091 A | | 4/1977 | |
| JP | 2008114210 A | | 5/2008 | |
| WO | WO2011002277 A1 | | 1/2011 | |
| WO | WO2019236249 A1 | | 12/2019 | |

OTHER PUBLICATIONS

EP0130319A2_ENG (Espacenet machine translation of Amlinger) (Year: 1985).*

EP0350677A1_ENG (Espacenet machine translation of Schuster) (Year: 1990).*

CN106582126A_ENG (Espacenet machine translation of Chen) (Year: 2017).*

International Application No. PCT/CN2020/101140 as prepared by the Chinese International Searching Authority filed on Jul. 9, 2020, 59 pages.

U.S. Appl. No. 17/012,857, TrackOne Bypass CON Application, filed Sep. 4, 2020, 148 pages.

International Application No. PCT/CN2020/100143 as prepared by the Chinese International Searching Authority filed on Jul. 3, 2020, 25 pages.

U.S. Appl. No. 17/002,500, TrackOne Bypass CON Application, filed Aug. 25, 2020, 61 pages.

International Application No. PCT/CN2020/100125 as prepared by the Chinese International Searching Authority filed on Jul. 3, 2020, 27 pages.

International Application No. PCT/CN2020/100115 as prepared by the Chinese International Searching Authority filed on Jul. 3, 2020, 22 pages.

U.S. Appl. No. 17/002,529, TrackOne Bypass CON Application, filed Aug. 25, 2020, 64 pages.

International Application No. PCT/CN2020/100119 as prepared by the Chinese International Searching Authority filed on Jul. 3, 2020, 29 pages.

U.S. Appl. No. 17/002,540, TrackOne Bypass CON Application, filed Aug. 25, 2020, 89 pages.

International Application No. PCT/CN2020/100120 as prepared by the Chinese International Searching Authority filed on Jul. 3, 2020, 28 pages.

U.S. Appl. No. 17/004,730, TrackOne Bypass CON Application, filed Aug. 27, 2020, 77 pages.

International Application No. PCT/CN2020/101142 as prepared by the Chinese International Searching Authority filed on Jul. 9, 2020, 29 pages.

U.S. Appl. No. 17/012,864, TrackOne Bypass CON Application filed on Sep. 4, 2020, 78 pages.

International Application No. PCT/CN2020/100144 as prepared by the Chinese International Searching Authority filed on Jul. 3, 2020, 24 pages.

U.S. Appl. No. 17/004,903, TrackOne Bypass CON Application, filed Aug. 27, 2020, 67 pages.

U.S. Appl. No. 17/004,903 Notice of Allowance, dated Nov. 6, 2020, 19 pages.

International Application No. PCT/CN2020/100122 as prepared by the Chinese International Searching Authority filed on Jul. 3, 2020, 34 pages.

U.S. Appl. No. 17/004,930, TrackOne Bypass CON Application, filed Aug. 27, 2020, 80 pages.

U.S. Appl. No. 17/004,930 Office Action-Restriction Requirement, dated Nov. 4, 2020, 6 pages.

International Application No. PCT/CN2020/100113 as prepared by the Chinese International Searching Authority filed on Jul. 3, 2020, 35 pages.

U.S. Appl. No. 17/004,971, TrackOne Bypass CON Application, filed Aug. 27, 2020, 75 pages.

U.S. Appl. No. 17/012,857, Non-Final Office Action, dated Nov. 24, 2020, 13 pages.

U.S. Appl. No. 17/002,500, Non-Final Office Action dated Dec. 8, 2020, 109 pages.

Kahm et al., 2018 "Lyapunov exponents with Model Predictive Control for exothermic batch reactors" IFAC-PapersOnline, 51, 417-422.

U.S. Appl. No. 17/002,540, Non-Final Office Action dated Dec. 30, 2020, 62 pages.

U.S. Appl. No. 17/004,930, Non-Final Office Action dated Jan. 26, 2021, 28 pages.

International Search Report and Written Opinion, International Application No. PCT/CN2020/101140 dated Dec. 21, 2020, 11 pages.

International Search Report and Written Opinion, International Application No. PCT/CN2020/100143 dated Dec. 21, 2020, 9 pages.

International Search Report and Written Opinion, International Application No. PCT/CN2020/100125 dated Dec. 23, 2020, 9 pages.

International Search Report and Written Opinion, International Application No. PCT/CN2020/100115 dated Dec. 16, 2020, 11 pages.

International Search Report and Written Opinion, International Application No. PCT/CN2020/100119 dated Dec. 17, 2020, 9 pages.

International Search Report and Written Opinion, International Application No. PCT/CN2020/101142 dated Dec. 16, 2020, 11 pages.

International Search Report and Written Opinion, International Application No. PCT/CN2020/100144 dated Dec. 18, 2020, 10 pages.

U.S. Appl. No. 17/002,500, Final Office Action dated Feb. 8, 2021, 57 pages.

U.S. Appl. No. 17/004,971, Notice of Allowance, dated Feb. 8, 2021, 30 pages.

U.S. Appl. No. 17/012,857, Notice of Allowance, dated Mar. 1, 2021, 26 pages.

U.S. Appl. No. 17/002,540, Final Office Action, dated Mar. 26, 2021, 36 pages.

U.S. Appl. No. 17/004,730, Non-Final Office Action, dated Apr. 1, 2021, 30 pages.

U.S. Appl. No. 17/002,540, Non-Final Office Action dated Apr. 15, 2021, 89 pages.

U.S. Appl. No. 17/002,540, Notice of Allowance, dated Apr. 26, 2021, 21 pages.

U.S. Appl. No. 17/004,930 Notice of Allowance, dated Apr. 28, 2021, 35 pages.

U.S. Appl. No. 17/004,903 Notice of Allowance, dated May 17, 2021, 20 pages.

U.S. Appl. No. 17/002,529 Notice of Allowance, dated May 3, 2021, 30 pages.

U.S. Appl. No. 17/012,864, Notice of Allowance, dated Jun. 15, 2021, 56 pages.

U.S. Appl. No. 17/004,730, Notice of Allowance, dated Jun. 24, 2021, 30 pages.

U.S. Appl. No. 17/012,857, Notice of Allowance, dated Jun. 28, 2021, 21 pages.

U.S. Appl. No. 17/002,500, Notice of Allowance dated Jul. 8, 2021, 27 pages.

* cited by examiner

ETHYLENE OXIDE ADSORPTION TOWER AND RECOVERY SYSTEM, AND METHOD FOR RECOVERING ETHYLENE OXIDE

CROSS-REFERENCE TO RELATED PATENT APPLICATIONS

This application is a continuation of International Application No. PCT/CN2020/100125 filed on Jul. 3, 2020, which claims the benefit of Chinese Patent Application No. CN202010194449.1 filed on Mar. 19, 2020, Chinese Patent Application No. CN202020348760.2, filed on Mar. 19, 2020, Chinese Patent Application No. CN202020348776.3, filed on Mar. 19, 2020, and Chinese Patent Application No. CN202010194457.6, filed on Mar. 19, 2020, the entire contents of which are incorporated herein by reference in their entireties for all purposes.

TECHNICAL FIELD

The present disclosure relates to the technical field of sterilization technology, and more particularly, and more particularly to an ethylene oxide adsorption tower, an ethylene oxide recovery system, and a method for recovering ethylene oxide.

BACKGROUND

Ethylene oxide ("EO") is a broad-spectrum, high-efficiency sterilization agent with excellent sterilization performance. The ethylene oxide has strong penetrating power, can kill various microorganisms at normal temperature, and does not damage the sterilized items during sterilization. Currently, the ethylene oxide gas sterilization method is one of the most important low-temperature sterilization methods, and especially is most commonly used in hospitals.

After sterilization with the ethylene oxide gas, the gas used for sterilization must be exhausted (referred to as the "sterilization exhaust gas"). However, the ethylene oxide itself is toxic and flammable and explosive. Thus, the sterilization exhaust gas generated in the sterilizer is typically subject to decontamination treatment before discharge. Conventional treatments of ethylene oxide sterilization exhaust gas include the following. (1) A catalytic combustion method, in which the sterilization exhaust gas is converted to a non-toxic substance by catalytic combustion. However, because ethylene oxide is flammable and explosive, this treatment method has poses significant safety hazards during the treatment process. (2) An adsorption method, wherein the sterilization exhaust gas generates ethylene glycol by acid catalysis. This method is suitable for the processing of high-concentration ethylene oxide exhaust gas. However, this process is prone to error and may result in secondary pollution. (3) A low temperature recovery method, wherein the sterilization exhaust gas is condensed at −29° C. to recover the ethylene oxide. However, this method has high energy consumption and very high equipment requirements.

Accordingly, tools and techniques for the improved treatment and recovery of ethylene oxide from sterilization exhaust gas are provided.

SUMMARY

In one aspect, an ethylene oxide adsorption tower is provided. The ethylene oxide adsorption tower comprises: a tower body defining a gas channel extending longitudinally therein, the tower body further comprising a sidewall, wherein the sidewall of the tower body comprises a plurality of mounting holes that are disposed longitudinally along the sidewall and in communication with the gas channel, a bottom portion of the tower body comprising a first pipe in communication with the gas channel, and a top portion of the tower body comprising a second pipe in communication with the gas channel; a plurality of adsorption panels slidably coupled to the tower body through a corresponding respective mounting hole of the plurality of mounting holes, wherein each of the plurality of adsorption panels extends into the gas channel; a sealing door movably coupled to the sidewall of the tower body and configured to selectively fix each of the plurality of adsorption panels to the corresponding respective mounting hole of the plurality of mounting holes.

In another aspect, an ethylene oxide recovery system is provided. The ethylene oxide recovery system comprises: an ethylene oxide adsorption tower as described above; a first gas intake pipe coupled to the first pipe and configured to carry a gas containing ethylene oxide into the first pipe, thereby enabling the gas containing ethylene oxide to enter the gas channel; a first gas outtake pipe coupled to the second pipe and configured to discharge the gas after treatment by the gas channel from the second pipe; a second gas outtake pipe coupled to the first pipe; and a recovery system coupled to the second gas outtake pipe and configured to extract gas from the gas channel through the second gas outtake pipe and the first pipe, thereby recovering the ethylene oxide adsorbed by the adsorption material.

In yet another aspect, a method for recovering ethylene oxide is provided. The method comprises: obtaining, from a sterilizer, a sterilization exhaust gas; discharging the sterilization exhaust gas into a first gas intake pipe coupled to an ethylene oxide adsorption tower, the ethylene oxide adsorption tower comprising a gas channel; introducing the sterilization exhaust gas into the gas channel; passing, via a gas distributor of the ethylene oxide adsorption tower, the sterilization exhaust gas through a plurality of adsorption panels sequentially from bottom to top in the gas channel; adsorbing, via adsorption materials in the plurality of adsorption panels, ethylene oxide in the sterilization exhaust gas; discharging, via a second pipe, a residual gas, wherein the residual gas comprises the sterilization exhaust gas after it has passed through the plurality of adsorption panels; detecting a concentration of the ethylene oxide in the residual gas; stopping flow of the sterilization exhaust gas into the first pipe when the concentration of ethylene oxide exceeds a preset value; extracting desorbed gas in the gas channel through the first pipe, wherein desorbed gas includes ethylene oxide desorbed from the adsorption material; and storing the ethylene oxide in the desorbed gas in a gas storage tank.

These and other objects, advantages, purposes, and features will become apparent upon review of the following detailed description in conjunction with the drawings.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION OF THE EMBODIMENTS

Exemplary embodiments will be described hereafter with reference to the drawings to clearly and fully illustrate the technical solutions of the present disclosure. All other embodiments obtained by a person of ordinary skill in the art based on the embodiments in the present disclosure without creative efforts are within the scope of the present disclosure.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Figure 1:
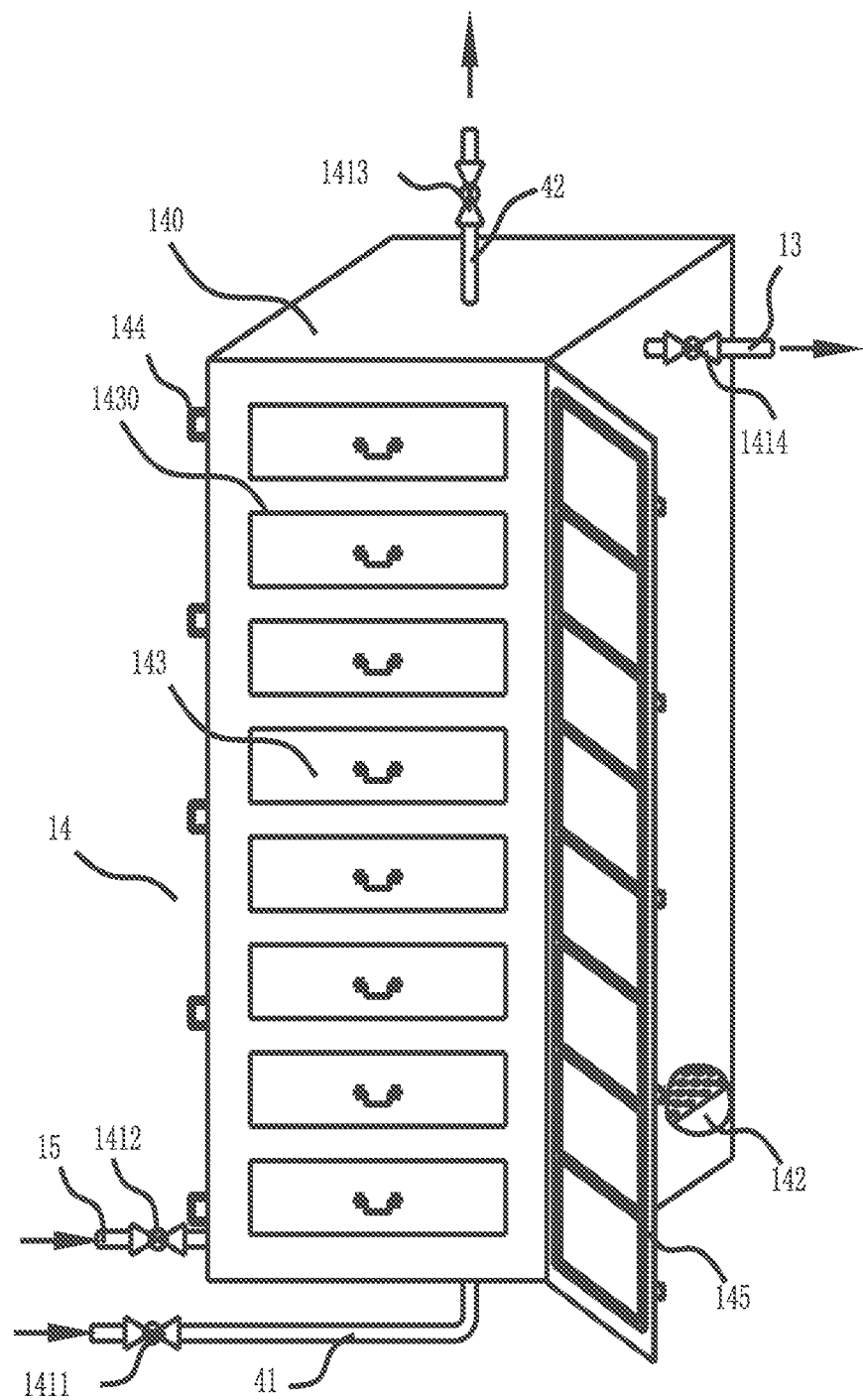
FIG. 1 is a perspective view of an adsorption tower in an embodiment of the present disclosure.

As shown in FIG. 1, according to an embodiment, an ethylene oxide (EO) adsorption tower 14 is provided. The EO adsorption tower 14 includes a tower body 140, a sealing door 145, and a plurality of adsorption panels 143. A gas channel (not shown) extending longitudinally is formed in the tower body 140, defined by the walls of the tower body 140. A bottom portion the tower body 140 includes a first pipe 41 in communication with a bottom portion the gas channel. The first pipe 41 may comprise a first valve 1411. A top portion the tower body 140 may comprise a second pipe 42 in communication with a top portion the gas channel, and the second pipe 42 may further comprise a second valve 1413. A plurality of adsorption panels 143 are positioned in the gas channel, spaced apart in a generally stacked arrangement, wherein the plurality of adsorption panels 143 are arranged serially from the top to a bottom portion the tower body 140 in a longitudinal direction. For example, in some embodiments, the plurality of adsorption panels 143 may be spaced evenly apart along a longitudinal length of the sidewall. Sterilization exhaust gas containing ethylene oxide may be introduced into the gas channel via the first pipe 41, and flow through the plurality of adsorption panels 143 sequentially. Once treated by passing through the plurality of adsorption panels 143, the treated exhaust gas (also referred to as "residual gas"), may be discharged from the gas channel via the second pipe 42.

In the illustrated embodiment, the cross-section of the gas channel may be generally rectangular in shape. A sidewall of the tower body 140 may comprise a plurality of mounting holes 1430 corresponding to each of the respective plurality of adsorption panels 143. Accordingly, the mounting holes 1430 may be spaced apart and arranged in a stacked arrangement longitudinally along the sidewall. Each of the plurality of mounting holes 1430 may be in communication with the gas channel. For example, in some embodiments, the plurality of mounting holes 1430 may be spaced evenly apart along the longitudinal length of the sidewall. The plurality of mounting holes 1430 may be slots into which a respective adsorption panel of the plurality of adsorption panels 143 may be inserted into the sidewall, and further, extending into the gas channel.

Figure 2:
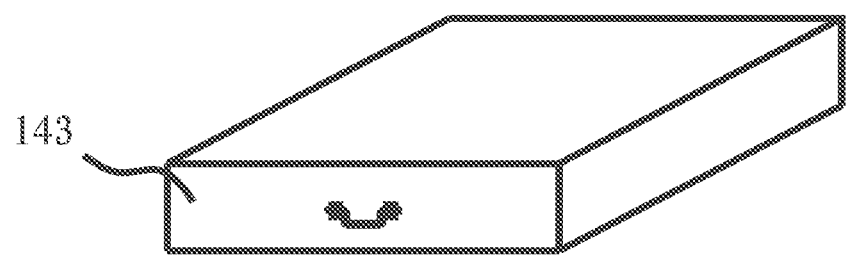
FIG. 2 is a perspective view of an adsorption panel of FIG. 1.

Referring to FIG. 2, the adsorption panel 143 may have a structure similar to a drawer, and may be slidably coupled to a corresponding respective mounting hole 1430 of the tower body 140 and configured to extend into the gas channel. In this way, each adsorption panel 143 can be slid out from the tower body 140, and may thereby be replaced or undergo maintenance. Each adsorption panel 143 may further comprise a handle to facilitate pulling.

Figure 3:
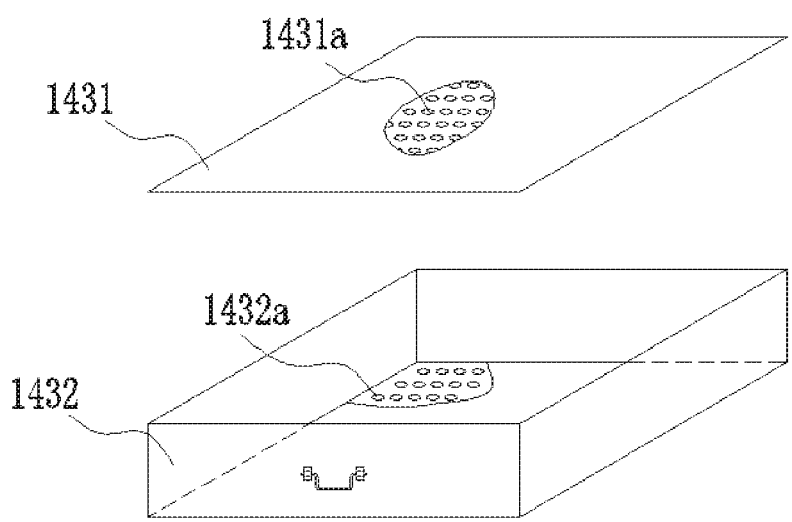
FIG. 3 is a perspective exploded view of the adsorption panel of FIG. 2.

Referring to FIG. 3, each individual adsorption panel of the plurality of adsorption panels 143 may include a support frame 1432, a holder 1431, and an adsorption material (not shown) held within the support frame 1432 for adsorbing the ethylene oxide. The support frame 1432 may be a rectangular frame having an opening at the top. The support frame 1432 may be configured to be inserted into a respective mounting hole of the plurality of mounting holes 1430. For example, each of the mounting holes 1430 may be a respective opening in the sidewall of the tower body 140, and configured to receive a respective adsorption panel 143. In some examples, the mounting hole 1430 may comprise a rail, guide, or track configured to guide the adsorption panel 143 into and out of the sidewall of the tower body 140. The support frame 1432 may further be configured to receive the adsorption material and/or the holder 1431. The holder 1431 may generally be a rectangular and/or square cover plate configured to cover the opening of the support frame 1432, thus fixing the adsorption material held in the support frame 1432, so as to prevent the adsorption material from being blown out of the support frame 1432 by gas flowing up through the stack of the plurality of adsorption panels 143. Both the support frame 1432 and the holder 1431 may further comprise ventilation to allow gas to pass through each adsorption panel of the plurality of adsorption panels 143. For example, a bottom plate of the support frame 1432 may comprise a plurality of first ventilation holes 1432a, and the holder 1431 may comprise a plurality of second ventilation holes 1431a. In some embodiments, the diameters of individual holes of the first plurality of ventilation holes 1432a and the second plurality of ventilation holes 1431a may be less than a particle size of the adsorption material, thereby preventing the adsorption material from being diffused outward through the ventilation holes by the flow of gas passing through the adsorption panel 143. In some embodiments, the adsorption material may be configured to adsorb and desorb the ethylene oxide in a sterilization exhaust gas. The adsorption material may include one or more of coconut shell activated carbon, columnar activated carbon, activated carbon fiber, silica gel, activated aluminum oxide, and a molecular sieve. In some embodiments, the sterilization exhaust gas may be a mixed gas mainly containing, for example, ethylene oxide and helium. In other embodiments, the sterilization exhaust gas may contain ethylene oxide and another diluent gas, as known to those skilled in the art.

Figure 4:
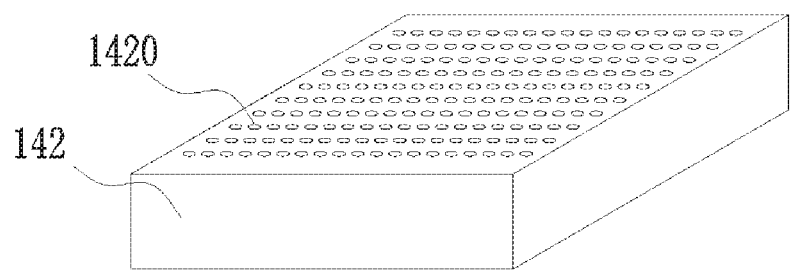
FIG. 4 is a perspective view of a gas distributor in an embodiment of the present disclosure.

Referring to FIG. 4, the EO adsorption tower 14 may further include a gas distributor 142. The gas distributor 142 may be disposed at a bottom portion of the gas channel and below the plurality of adsorption panels 143. The first pipe 41 may be coupled to the gas distributor 142. In some embodiments, the gas distributor 142 may be generally box-shaped, and comprise a plurality of third ventilation holes 1420 disposed at a top portion of the gas distributor 12, the plurality of third ventilation holes 1420 in communication with the first pipe 41 and the gas channel. The diameter of individual holes of the third plurality of ventilation holes 1420 may be less than a particle size of the adsorption material. Thus, the adsorption material may be prevented from leaking into the gas distributor 142. The gas distributor 142 may be configured to disperse gas, diffusing the gas uniformly into the gas channel, and to allow the gas to come into contact with the adsorption material in an evenly dispersed manner.

Referring to FIG. 1 again, a sealing door 145 may be moveably coupled to the sidewall of the EO adsorption tower 14. The sealing door 145 may be configured to have an open state and a closed state. In the closed state, the sealing door 145 may be configured to selectively fix the plurality of adsorption panels 143 to respective mounting holes of the plurality of mounting holes 1430. Thus, the sealing door 145 may be opened (e.g., in an open state) and closed (in a closed state). In some embodiments, the sealing door 145 may be hinged at the sidewall (e.g., coupled to the sidewall via hinges). When the sealing door 145 is closed, the plurality of adsorption panels 143 may be fixed to respective mounting holes of the plurality of mounting holes 1430, thereby preventing the adsorption panel 143 from sliding out of the tower body 140. When the sealing door 145 is opened, the plurality of adsorption panels 143 are able to be removed from the tower body 140 or inserted into a respective mounting hole of the tower body 140.

Figure 5:
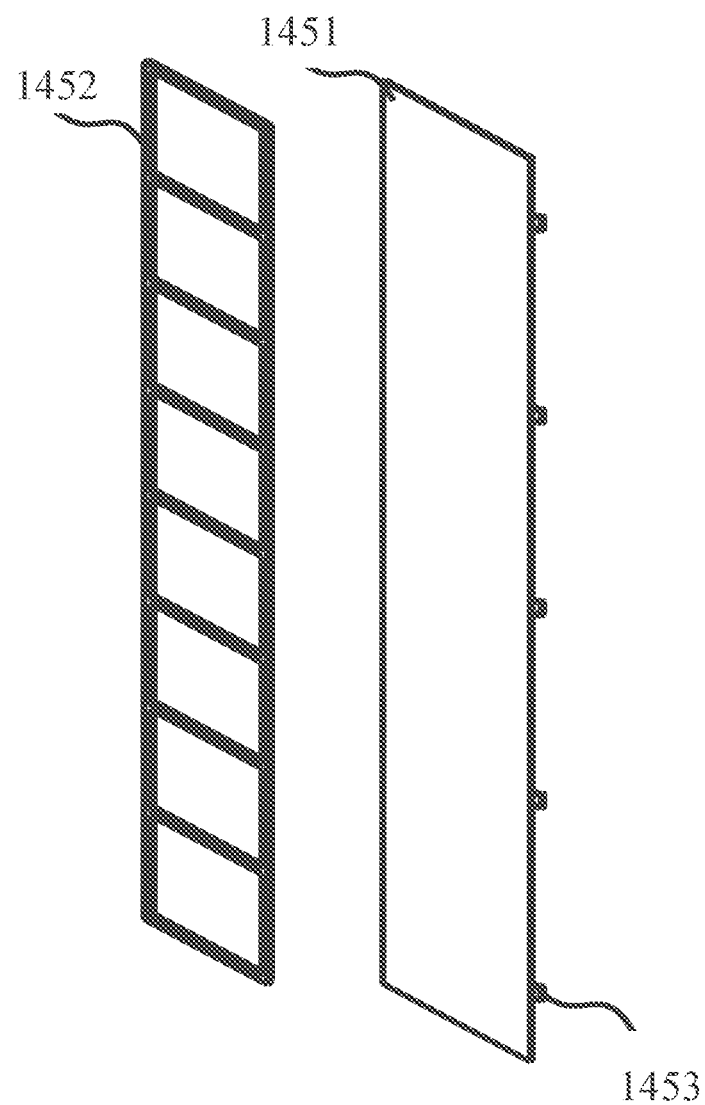
FIG. 5 is an exploded view of a sealing door of FIG. 1.

Referring to FIG. 5, the sealing door 145 may include a door plate 1451 and a sealing strip 1452. A longitudinal edge of one side of the door plate 1451 may be pivotally coupled to the sidewall of the tower body 140, and a longitudinal edge of the other side of the door plate 1451 may comprise one or more couplers, such as a plurality of snap fittings 1453. A corresponding edge of the tower body 140 may comprise a respective plurality of fixing rings 144 configured to receive the plurality of snap fitting 1453. The plurality of snap fittings 1453 may, thus, be snapped to a respective fixing ring of the plurality of fixing rings 144 to ensure that the sealing door 145 closes, forming a seal with the tower body 140, and further that the seal is maintained between the sealing door 145 and the tower body 140. Accordingly, in some embodiments, the sealing strip 1452 may be adhered on a side of the door plate 1451 facing the tower body 140. In some embodiments, the sealing strip 1452 may be arranged to create an outline corresponding to each of the plurality of adsorption panels 143. Thus, the sealing strip 1452 may be configured to create a seal with the tower body 140 and furthermore around each of the plurality of adsorption panels 143. Thus, any gaps between a mounting hole and an adsorption panel inserted into the mounting hole may be sealed by the sealing strip 1452 when the sealing door 145 is closed. In some examples, the sealing strip 1452 may be made of rubber and include a plurality of sealing rings corresponding to the edges of each of the plurality of adsorption panels 143. When the sealing door 145 is closed, the sealing strip 1452 may press against the sidewall of the tower body 140, as well as surround each of the plurality of mounting holes 1430, respectively sealed by corresponding sealing rings, such that the gas channel is isolated from external environment, and preventing leakage of gas from around the edges of the sealing door 145 and/or the respective edges of the plurality of adsorption panels 143.

Referring to FIG. 1 again, the EO adsorption tower 14 may further include a water heat exchange system configured to cool or heat the tower body 140. The water heat exchange system may include a water inlet pipe 15 located at the bottom portion the tower body 140, a water outlet pipe 13 located at the top portion the tower body 140, and a water circulation interlayer located in the tower body 14. The water circulation interlayer may be coupled to the water inlet pipe 15 and the water outlet pipe 13, respectively. The water inlet pipe 15 may further comprise a valve 1412, and the water outlet pipe 13 may comprise a valve 1414. Thus, cold water or hot water may enter the water circulation interlayer through the water inlet pipe 15 and may be discharged from the water circulation interlayer through the water outlet pipe 13.

An assembly process of the EO adsorption tower 14 according to various embodiments is described below.

In step S1, a tower body 140, as previously described, may be provided, a sealing door 145 being coupled to the tower body 140.

In step S2, a plurality of adsorption panels 143 are provided. Specifically, adsorption material may be disposed in a support frame 1432, and a holder 1431 may be configured to cover an opening of the support frame 1432. Specifically, the holder 1431 may be configured to press and fix the adsorption material in the support frame 1432, thereby preventing the adsorption material from being blown out of the adsorption panel 143, while ensuring gases are able to flow through the adsorption panel 143.

In step S3, the plurality of adsorption panels 143 may be slidably coupled to a respective mounting hole of the plurality of mounting holes 1430 of the tower body 140, as previously described above.

In step S4, the gas distributor 142 may be coupled to the bottom portion of the gas channel, below the adsorption panels 143.

In step S5, the sealing door 145 may be closed, creating a seal with the tower body. In some embodiments, a seal may be created by the pressing of a sealing strip 1452 against the tower body 140 and/or a plurality of sealing rings around the edges of each of the plurality of adsorption panels 143. The sealing door 145 may be kept in a closed state via a plurality of snap fittings 1453. Thus, the sealing door 145 may be configured to prevent the plurality of adsorption panels 143 from sliding out of the tower body 140, and further to seal in gas in the gas channel while closed.

The assembly of the EO adsorption tower 14 is thus completed.

The EO adsorption tower 14 of this embodiment has a simple structure, and uses the principles of physical adsorption and desorption to separate the ethylene oxide in the ethylene oxide sterilization exhaust gas, which can save resources. The adsorption material may be placed within the drawer-like adsorption panels of the plurality of adsorption panels 143, allowing adsorption material to be replaced as needed. The assembly and disassembly of each of the plurality of adsorption panels 143 and the tower body 140 are also very convenient. In addition, the sealing door 145 allows the adsorption and desorption reactions to proceed in air-tight conditions, which improves production efficiency.

Figure 6:
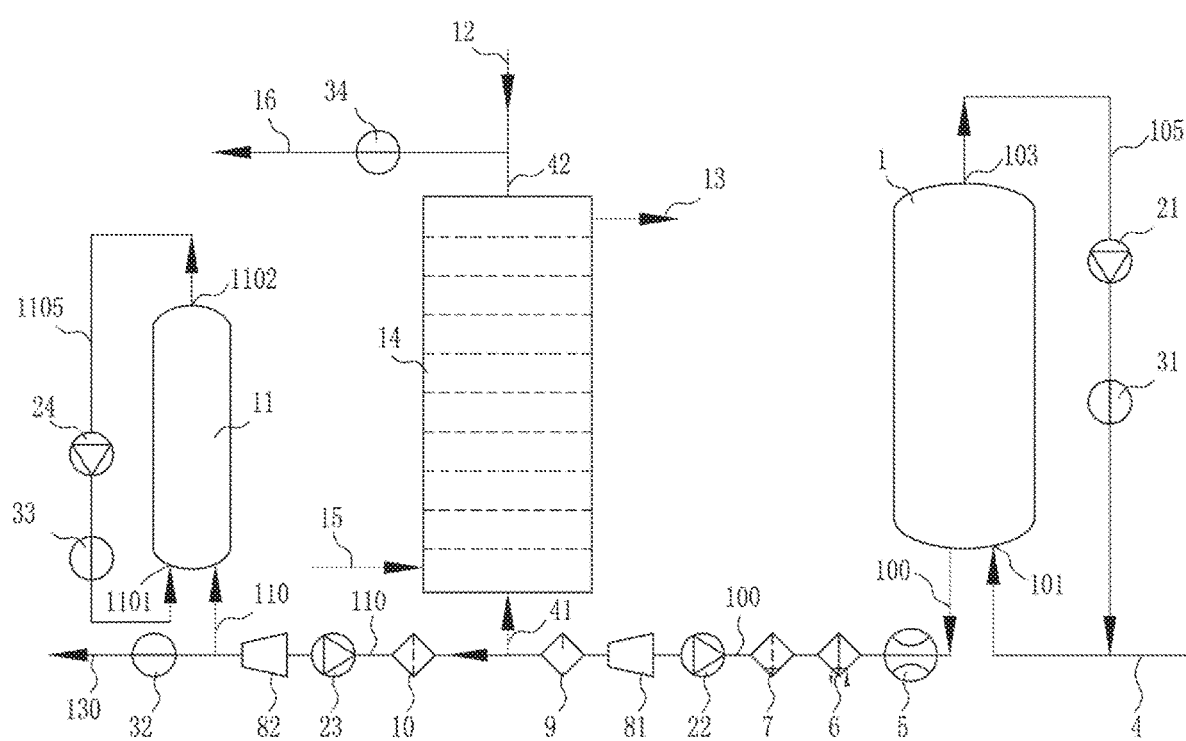
FIG. 6 is a schematic view of a sterilization system in an embodiment of the present disclosure.

Referring to FIG. 6, according to an embodiment, an ethylene oxide recovery system is provided. The EO recovery system includes the above-described EO adsorption tower 14, a sterilizer 1, and a recovery assembly.

The EO recovery system may include a first gas intake pipe 100 coupled to the first pipe 41. The first gas intake pipe 100 may be configured to carry gas containing EO to be processed (e.g., exhaust sterilization gas) to the first pipe 41. The first gas intake pipe 100 may be coupled to the sterilizer 1, and the gas containing EO discharged from the sterilizer 1 (e.g., sterilization exhaust gas) may be fed into the gas channel of the EO adsorption tower 14 through the first gas intake pipe 100 and the first pipe 41.

The EO recovery system may further include a first gas outtake pipe 16 coupled to the second pipe 42. The first gas outtake pipe 16 may be configured to carry the residual gas discharged from the second pipe 42 to the next processing step to continue the gas treatment process. Residual gas, as used herein, may refer to sterilization exhaust gas that has been passed through the plurality of adsorption panels 143 as previously described. Further, a first EO detector 34 may be coupled to the first gas outtake pipe 16, the first EO detector 34 configured to detect the concentration of ethylene oxide in the residual gas discharged from the EO adsorption tower 14.

The recovery assembly may be coupled to the first pipe 41, via the second gas outtake pipe 110. The recovery assembly may be configured to desorb and recover EO from the adsorption material in the plurality of adsorption panels 143. Specifically, the recovery assembly includes a gas storage tank 11, and a first gas extractor 23 coupled to the second gas outtake pipe 110. The first gas extractor 23 may be located upstream of the gas storage tank 11. The first gas extractor 23 may be configured to evacuate the gas channel of the adsorption tower 14, such that the EO desorbed from the adsorption material can be recovered into the gas storage tank 11. Evacuation of the gas channel may include, without limitation, creating a pressure differential between the gas channel and the gas storage tank 11, such as via a vacuum, to cause EO in the adsorption material to be desorbed and evacuated into the gas storage tank 11. Thus, in some embodiments, the first gas extractor 23 may be a vacuum pump.

Further, a filter 10 and a first compressor 82 are also coupled to the second gas outtake pipe 110. The filter 10 may be located downstream of the first pipe 41 and upstream of the first gas extractor 23. The first compressor 82 may be located downstream of the first gas extractor 23 and upstream of the gas storage tank 11. In some examples, the first compressor 82 may be a booster pump. Furthermore, the recovery assembly may include a first circulation pipeline 1105. The first circulation pipeline 1105 may couple a gas inlet 1101 to a gas outlet 1102 of the gas storage tank 11. A second gas extractor 24 and a second EO detector 33 may be coupled to the first circulation pipeline 1105. In some examples, the second gas extractor 24 may similarly be a vacuum pump. By activating the second gas extractor 24, the gas in the gas storage tank 11 may flow through the first circulation pipeline 1105. The second EO detector 33 may detect the concentration of EO in the gas storage tank 11.

Furthermore, the EO recovery system may further include a second gas intake pipe 12 coupled to the second pipe 42. The second gas intake pipe 12 may be configured to fill the gas channel of the tower body 140 with a desorbing gas through the second pipe 42. In some examples, the desorbing gas may be nitrogen. The EO recovery system may further include a third gas outtake pipe 130 coupled to the first pipe 41. In some embodiments, the desorbing gas may be discharged from the first pipe 41 into the third gas outtake pipe 130 for further downstream processing.

Accordingly, the third gas outtake pipe 130 may be coupled to the second gas outtake pipe 110. In some embodiments, the third gas outtake pipe 130 and the second outtake pipe 110 may be coupled at a point that is between the first gas extractor 23 and the gas storage tank 11, downstream of the first compressor 82 and upstream of the gas storage tank 11. A third EO detector 32 may be coupled to the third gas outtake pipe 130 and configured to detect the EO concentration of the gas in the third gas outtake pipe 130.

In some embodiments, the EO recovery system may further include a cooling and heating system. The cooling and heating system may be coupled to the water inlet pipe 15 and the water outlet pipe 13 to provide hot water circulation or cold water circulation for the water heat exchange system in the tower body 140. The cooling and heating system may include a water storage tank located outside the tower body 140. In some examples, the water storage tank may be an electrical heating water tank. The water storage tank may be coupled to the water inlet pipe 15 and the water outlet pipe 13, respectively through the water circulation pipe, which may provide cooling circulation and/or a heating circulation for the tower body 140.

The operation of the EO recovery system according to various embodiments is described below.

While EO is being adsorbed by the adsorption material, the valve 1411 in the first pipe 41, the valve 1412 in the water inlet pipe 15, the valve 1413 in the second pipe 42, and the valve 1414 in the water outlet pipe 13 may be opened. The gas to be processed (such as the EO sterilization exhaust gas) may enter the gas distributor 142 of the adsorption tower 14 through the first gas intake pipe 100 and the first pipe 41. Cooled water (20° C. to 30° C.) may be continuously supplied into the water heat exchange system of the adsorption tower 14 through the water inlet pipe 15, and may be discharged through the water outlet pipe 13, thereby cooling the adsorption tower 14. When sterilization exhaust gas enters the adsorption tower 14, the sterilization exhaust gas may be evenly diffused into the gas channel via the gas distributor 142. The sterilization exhaust gas (or other gas to be treated) may then sequentially flow through the adsorption material of each of the plurality of adsorption panels 143, rising from the bottom of the gas channel to the top of the gas channel. The adsorption material may thus adsorb EO in the sterilization exhaust gas as it passes through the respective adsorption panel. The residual gas remaining after passing through the plurality of adsorption panels 143 may be discharged to the first gas outtake pipe 16 through the second pipe 42. After the plurality of adsorption panels are saturated, valve 1411 and valve 1413 may be closed, valve 1412 and the valve 1414 may be closed, and the flow of sterilization exhaust gas and cooled water to the adsorption tower 14 stopped.

To desorb the EO adsorbed by the adsorption material, valve 1411, valve 1412, and valve 1414 are opened, and valve 1413 is closed. The first gas extractor 23 may then be activated. The heated water (60° C. to 90° C.) may continuously be supplied to the water heat exchange system of the adsorption tower 14 through the water inlet pipe 15, and then discharged through the water outlet pipe 13, thereby heating the adsorption tower 14. Under the action of the first gas extractor 23, EO may be desorbed from the adsorption material, and enter the gas storage tank 11 through the first pipe 41 and the second gas outtake pipe 110 for storing.

When the rate of thermal desorption of the adsorption material decreases to a first threshold, valve 1413 may be opened, and the gas channel filled with nitrogen via the second gas intake pipe 12 and the second pipe 42, aiding in desorption. The desorbing gas (e.g., nitrogen) may be discharged through the first pipe 41 and the third gas outtake pipe 130.

When the desorption of the adsorption material is completed, adsorption may be performed again.

In some embodiments, the water inlet pipe 15 and the water outlet pipe 13 may each be coupled to the water storage tank to circulate water. In some embodiments, the water used herein may be rainwater collected and stored by a rainwater collector, and may be heated by a renewable energy source, such as a solar power system.

In the present embodiment, the sterilizer 1 may be an EO sterilizer. The sterilizer 1 may be coupled to the first pipe 41 through the first gas intake pipe 100. The EO recovery system further includes a third gas intake pipe 4 coupled to the sterilizer 1 and configured to fill the sterilizer 1 with EO sterilization gas. The EO recovery system further includes a second circulation pipeline 105 coupled to a gas inlet 101 and the gas outlet 103 of the sterilizer 1, respectively. The second circulation pipeline 105 may comprise a third gas extractor 21 and a fourth EO detector 31. The third gas extractor 21 may be a vacuum pump. By activating the third gas extractor 21, the gas in the sterilizer 1 may be circulated via the second circulation pipeline 105 in the sterilization chamber 1. The fourth EO detector 31 may be configured to detect the concentration of EO in the sterilizer 1.

The sterilizer 1 may thus provide a sterilization exhaust gas for subsequent recovery processing. The concentration of EO in the sterilization exhaust gas may be adjusted in the sterilizer 1, which in turn may allow EO gas concentration to be detected more easily during subsequent processing.

In some embodiments, following a flow direction of the gas flowing in the first gas intake pipe 100, a flow meter 5, a heat exchanger 6, a gas-liquid separator 7, a fourth gas extractor (vacuum pump) 22, a second compressor 81, and a gas dryer 9 may be sequentially coupled to the first gas intake pipe 100. The above-mentioned components may be configured to condition the sterilization exhaust gas for processing. For example, in some embodiments, the sterilization exhaust gas may be undergo pre-cooling, dehumidifying, and drying process. The above components may further be configured to control and monitor the gas intake flow, which can better promote the adsorption and desorption process.

The EO recovery system may further include a gas chromatography detection system, which may be configured to detect the concentration of the EO in the sterilization exhaust gas and/or EO sterilization gas used in the sterilizer 1.

It should be noted that, in order to control the flow direction of the gas in each of the above pipes, each pipe may be provided with a valve as needed. For example, in some embodiments, the valves may be electronic control valves.

Figure 7:
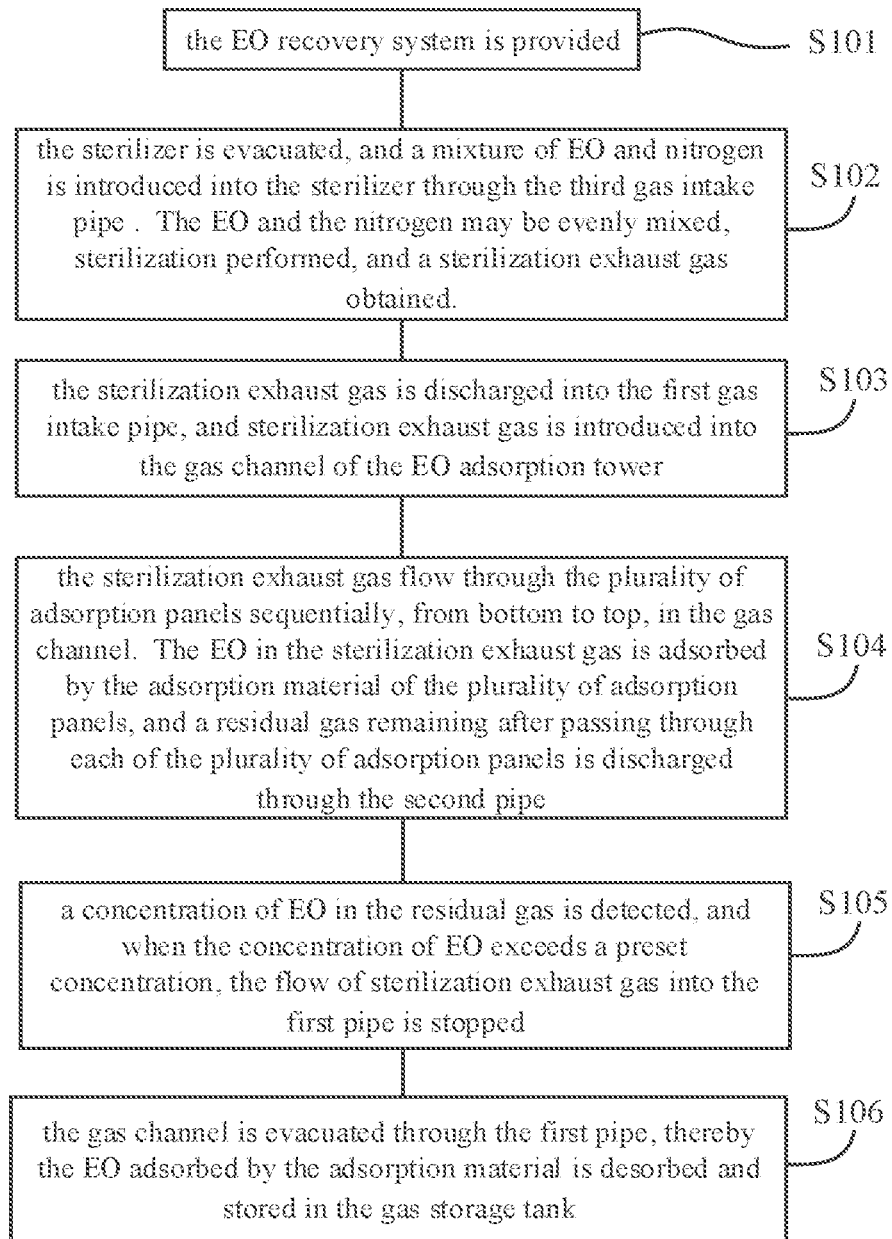
FIG. 7 is a flowchart of a method for recovering ethylene oxide in an embodiment of the present disclosure.

Referring to FIG. 7, a method for recovering EO is provided, according to some embodiments. The method includes the following:

In step S101, the above described EO recovery system is provided.

In step S102, the sterilizer 1 may be evacuated, and a mixture of EO and nitrogen is introduced into the sterilizer 1 through the third gas intake pipe 4. The EO and the nitrogen may be evenly mixed, sterilization performed, and a sterilization exhaust gas obtained. In some embodiments, a volume ratio of EO and nitrogen introduced into the sterilizer 1 may range from 1:9 to 4:6, and a concentration of the EO in the sterilization exhaust gas may range from 1 volume percent (vol %) to 50 vol %.

In step S103, the sterilization exhaust gas may be discharged into the first gas intake pipe 100, and sterilization exhaust gas may be introduced into the gas channel of the EO adsorption tower 14.

In step S104, the sterilization exhaust gas may flow through the plurality of adsorption panels 143 sequentially, from bottom to top, in the gas channel. The EO in the sterilization exhaust gas may thus be adsorbed by the adsorption material of the plurality of adsorption panels 143, and a residual gas remaining after passing through each of the plurality of adsorption panels may be discharged through the second pipe 42. Optionally, in step S104, the EO adsorption tower may be cooled, as previously described.

In step S105, a concentration of EO in the residual gas may be detected, and when the concentration of EO exceeds a preset concentration, the flow of sterilization exhaust gas into the first pipe 41 may be stopped.

In step S106, the gas channel may be evacuated through the first pipe 41, thereby the EO adsorbed by the adsorption material may be desorbed and stored in the gas storage tank 11. Optionally, in step S106, the EO adsorption tower may be heated.

The method for recovering the above EO sterilization exhaust gas will be described in detail below with reference to embodiments of various experimental implementations.

In the following embodiments, the EO may be industrial EO with a purity of 99.99%; the nitrogen may be industrial nitrogen with a purity of 99.9%; the adsorption materials include coconut shell activated carbon, 13× molecular sieve and 4 A molecular sieve.

The method for detecting the EO content in sterilization exhaust gas may comprise the following procedures and tools:

(1) Gas chromatography detection: sampling and testing Instrument: Gas chromatograph Agilent 7890B;

Chromatography column: FFAP quartz capillary column (25 m×0.25 mm×0.25 μm);

Temperature: The column temperature being maintained at 45° C. for 7 minutes, increasing the temperature to 120° C. at 15° C./min, and maintaining the temperature for 7 minutes, sample inlet 130° C., detector 150° C.;

Carrier gas: Nitrogen 2 mL/min, Hydrogen 35 mL/min, Air 400 mL/min;

Sample introduction: automatic, gas sample 1 mL;

Detector: hydrogen flame detector (FID).

2. EO concentration detector: online real-time detecting the concentration of the EO gas in pipelines, and the following detectors can be arbitrarily selected and applied in the present disclosure.

Instrument: online EO concentration detector thermal conductivity MIC-500s-ETO (0-99% vol, resolution 0.01% vol);

Fixed EO detector alarm electrochemistry JSA5-ETO-AX (0-100 ppm, resolution 0.01 ppm);

Online EO concentration detector (PID) (0-2000 ppm, resolution 0.1 ppm).

Example 1

(1) The fourth gas extractor 22 was used to evacuate the sterilizer 1, creating vacuum pressure in the sterilizer 1 ranging from −0.050 MPa to −0.086 MPa, for example, to −0.08 MPa, and pure EO gas was introduced into the sterilizer 1 through the third gas intake pipe 4 until the pressure in the sterilizer 1 reaches −0.013 MPa. Nitrogen was then introduced until the pressure in the sterilizer 1 reached 0.05 MPa. Then, the gases in the sterilizer 1 were mixed uniformly through the third gas extractor 21 and the second circulation pipeline 105 to complete the sterilization and to obtain the resulting sterilization exhaust gas. The sterilization exhaust gas was a mixed gas mainly containing EO and nitrogen. The concentration of EO in the sterilizer 1 detected by the fourth EO detector 31 was 44.18 vol %. At the same time, the gas in the sterilizer 1 was sampled by a sampling device and a gas sampling bag, and the concentration of EO in the sterilization exhaust gas in the sterilizer 1 detected by the gas chromatograph was 788.6 mg/L.

(2) The fourth gas extractor 22 was used to extract the sterilization exhaust gas from the sterilizer 1 via the first gas intake pipe 100. The flow meter 5 was used to detect and control a flow rate of the sterilization exhaust gas. The sterilization exhaust gas was cooled by the heat exchanger 6. The gas-liquid separator 7 separated water from the cooled sterilization exhaust gas. The separated EO sterilization exhaust gas was pressurized by the second compressor 81, and carried through the gas dryer 9 to the EO adsorption tower 14. The adsorption material in the adsorption tower 14 was coconut shell activated carbon. The cooling and heating system was operated continuously to feed the cooled water into the water inlet pipe 15 of the adsorption tower 14, which allowed the adsorption tower to be cooled a temperature ranging from 20° C. to 30° C. After the separated EO sterilization exhaust gas was passed through plurality of adsorption panels 143 of the EO adsorption tower 14, the residual gas (containing the EO that had not been adsorbed and nitrogen) was discharged through the second pipe 42 and the first gas outtake pipe 16, and the adsorption process was completed. The first EO detector 34 monitored the concentration of EO in the first gas outtake pipe 16 in real-time. At the same time, the gas in the sterilizer 1 was sampled by the sampling device and the gas sampling bag, and the concentration of EO in the discharged sterilization exhaust gas was detected by the gas chromatograph.

(3) When the adsorbent (e.g., adsorption material) reached a saturation point, for example, when it was detected that the concentration of EO in the discharged residual gas increases to 100 ppm, or the concentration of EO in the discharged gas increases to a range from 6 vol % to 21 vol %, the flow of sterilization exhaust gas into the adsorption tower 14 through the first gas intake pipe 100 was stopped, the feeding of the cooled water into the water intake pipe 15 was stopped, and the desorption was initiated. The cooling and heating system continuously fed the 80° C. hot water into the water inlet pipe 15 to heat the adsorption tower 14, and the temperature of the adsorption tower was raised to a range from 60° C. to 90° C. The first gas extractor 23 evacuated the gas channel of the adsorption tower 14 by creating a vacuum condition within the gas channel. This caused the EO adsorbed in the adsorption material to be desorbed, and the desorbed EO to enter the second gas outtake pipe 110. The desorbed high-concentration EO gas was compressed and stored in the EO gas storage tank 11 by the first compressor 82. When the gas channel of the EO adsorption tower 14 was subject to the vacuum ranging in pressure from −0.065 MPa to −0.086 MPa, the thermal desorption capacity was reduced, and the amount of the gas entering the EO gas storage tank 11 was also reduced. At this time, nitrogen gas was introduced into the gas channel through the second gas intake pipe 12 and the second pipe 42 to initiate the blow-off process. The desorbed high-concentration EO gas was stored in the EO gas storage tank 11. The gas in the EO gas storage tank 11 was circulated through the second gas extractor 24 and the first circulation pipeline 1105, and the concentration of EO was detected by the second EO detector 33. At the same time, the gas in the sterilizer 1 was sampled by the sampling device and the gas sampling bag, and the concentration of EO in the recovered gas was detected by the gas chromatograph. The concentration of EO in the gas storage tank was detected through the first circulation pipeline reaches a range from 89.34 vol % to 99.99 vol %.

Figure 8:
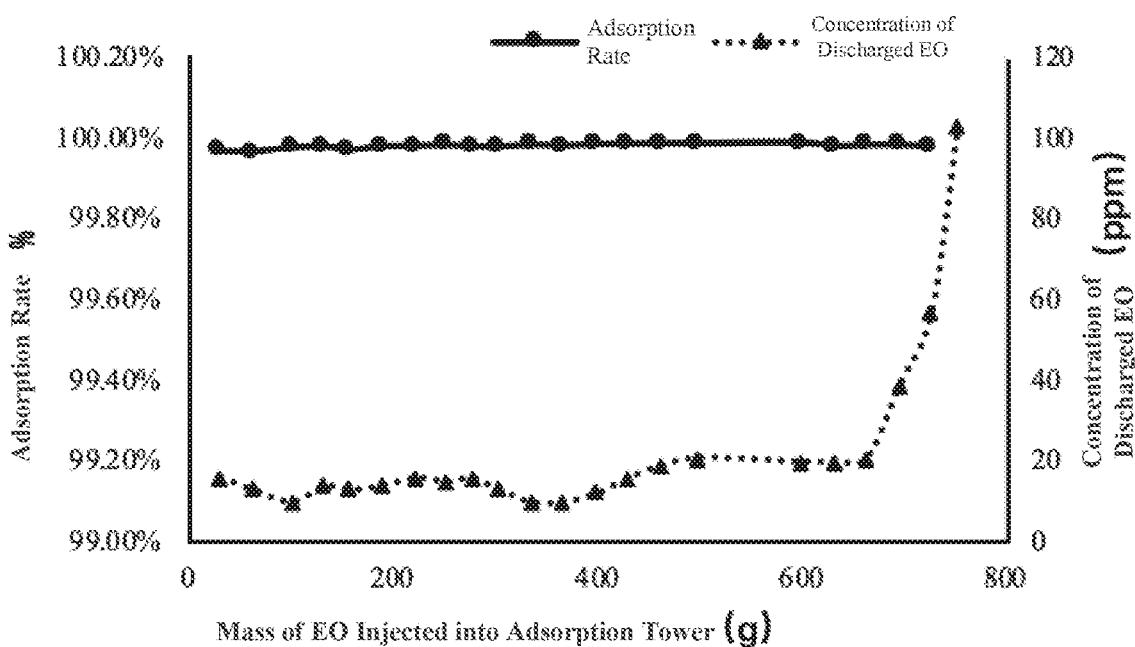
FIG. 8 is a graph illustrating efficiency of ethylene oxide adsorption by coconut shell activated carbon.

FIG. 8 the illustrates the real time concentration of EO in the discharged residual gas after the EO in the sterilization exhaust gas is adsorbed by coconut shell activated carbon adsorption material. The concentration of EO was online-monitored by the EO detector in real time. As shown in FIG. 8, the EO in the adsorption tower 14 was adsorbed by the plurality of adsorption panels comprising coconut shell activated carbon as adsorption material. The concentration of EO in the discharged residual gas after adsorption was less than 20 ppm, which indicates that coconut shell activated carbon has high adsorption efficiency.

Figure 9:
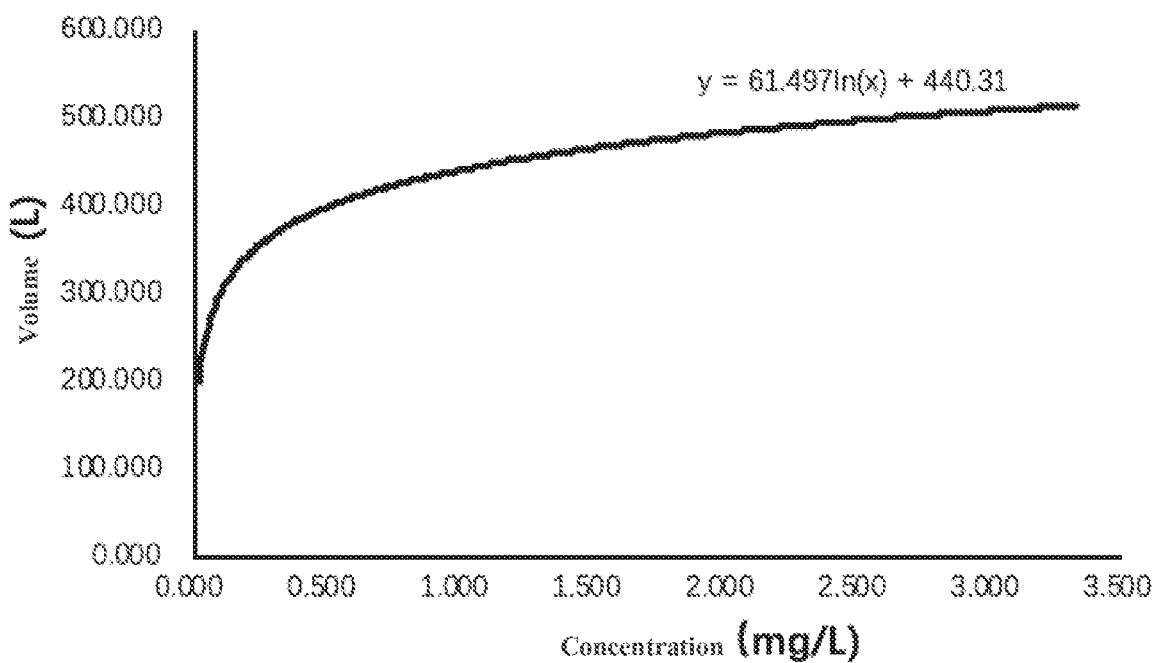
FIG. 9 is a graph illustrating adsorption of ethylene oxide by coconut shell activated carbon.

It can be seen from the curve of the adsorption of EO by coconut shell activated carbon in FIG. 9 that coconut shell activated carbon has a high adsorption efficiency for EO at the beginning of the adsorption. As the amount of EO adsorbed by the adsorbent increased, especially when the adsorption amount approached the saturation limit, the adsorption efficiency of EO decreased, the adsorption amount decreased, and the concentration of EO in the discharged residual gas increased.

The gas chromatography detection indicated that after the sterilization exhaust gas with the concentration of EO of 788.6 mg/L is adsorbed by coconut shell activated carbon, the concentration of EO in the discharged residual gas was about 10 ppm. Therefore, the adsorption efficiency is above 99.99%, and the adsorption rate (the percentage of the absorbed EO and the coconut shell activated carbon) is 10.61%.

Figure 10:
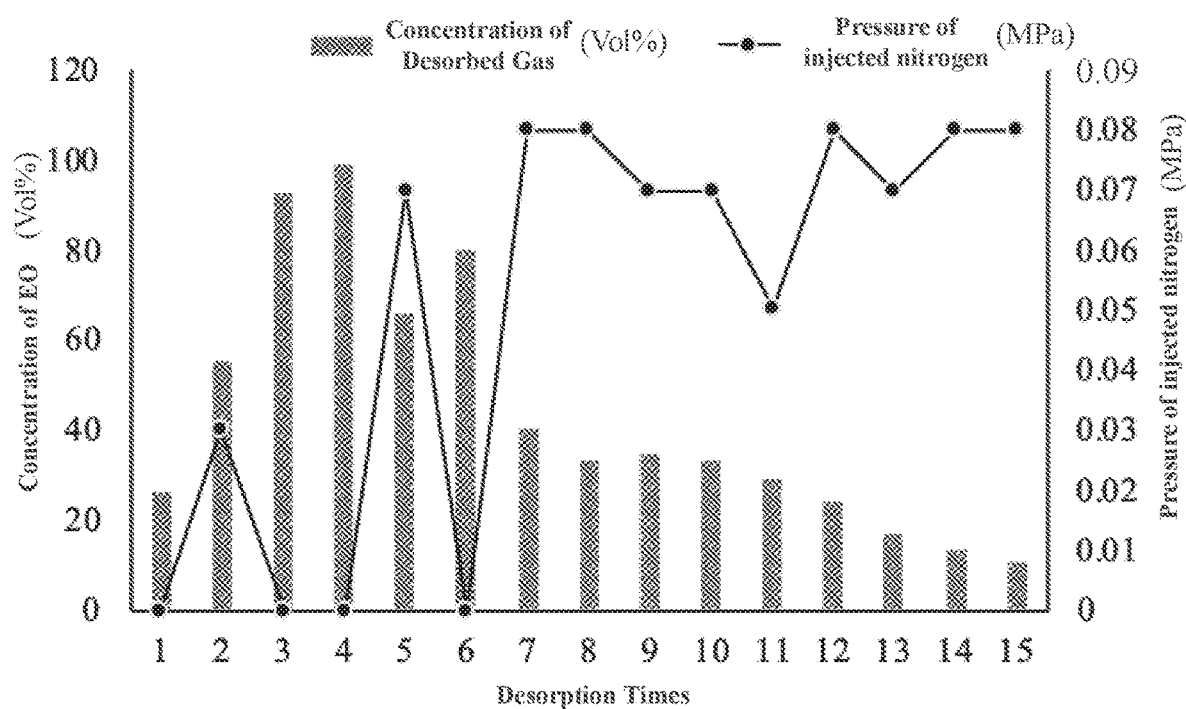
FIG. 10 is a graph illustrating a concentration of ethylene oxide desorbed and recovered by coconut shell activated carbon.
Figure 11:
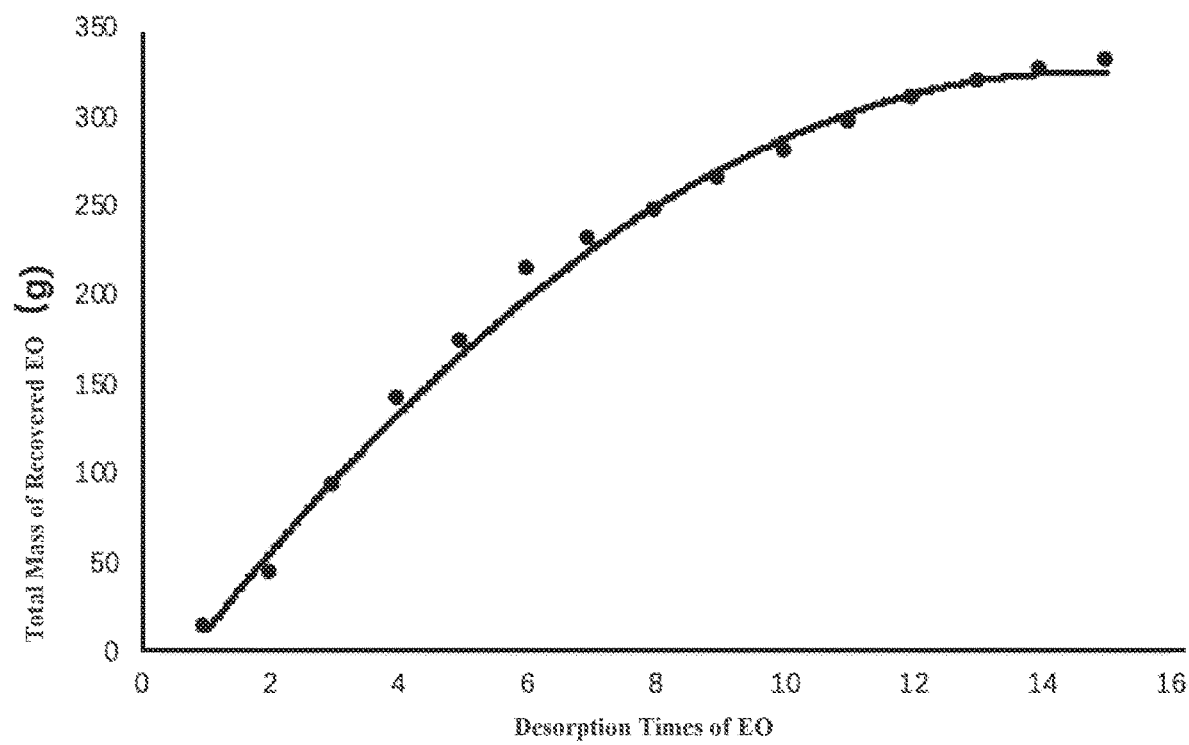
FIG. 11 is a graph illustrating a cumulative mass of ethylene oxide desorbed and recovered by coconut shell activated carbon.
Figure 12:
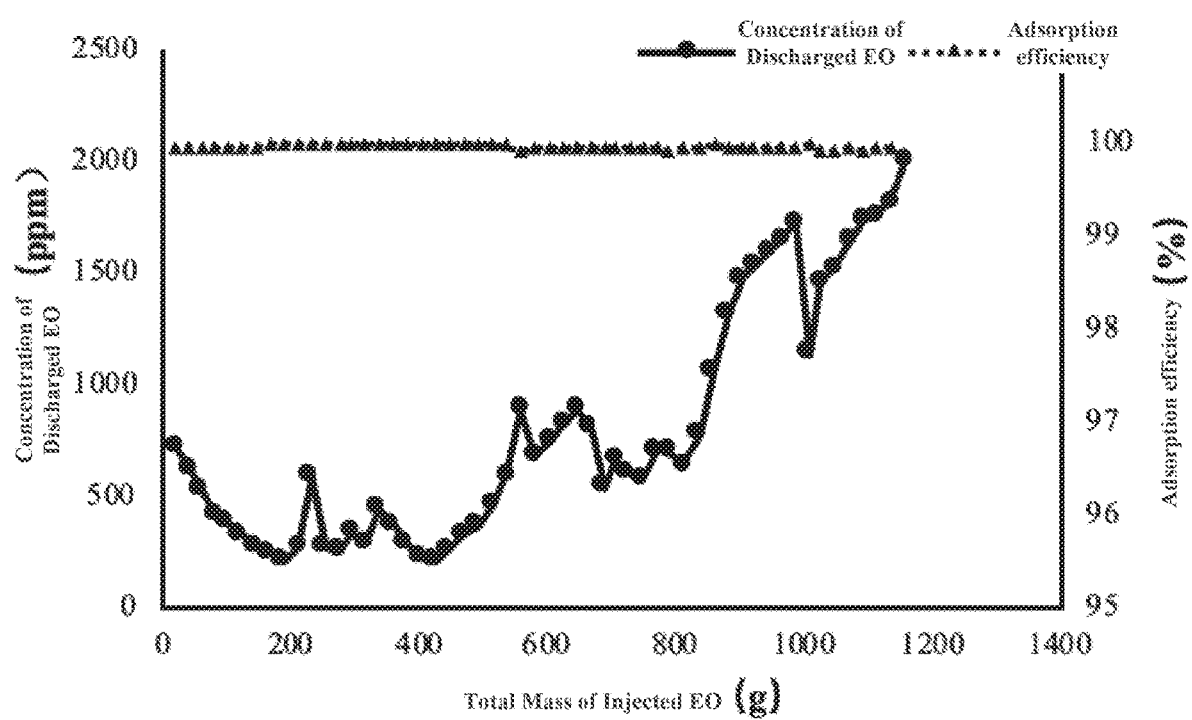
FIG. 12 is a graph illustrating efficiency of ethylene oxide adsorption by 13× molecular sieve.

FIG. 10 illustrates the real time concentration of EO in the recovered gas, online-monitored by the EO detector in real time. With the thermal cycle and vacuum desorption, EO is continuously desorbed from coconut shell activated carbon. The concentration of EO continues to increase, with the highest recovery concentration of EO reaching 99.99 vol %. The recovery concentration detected by gas chromatography is 1755.4 mg/L. When a vacuum pressure in the adsorption tower reaches −0.08 MPa, it was necessary to fill nitrogen to perform the desorption sequentially. At this time, the concentration of EO obtained by the desorption began to decrease. By the seventh desorption, the concentration of EO obtained by the desorption was close to the concentration of EO in the sterilizer, at this time the average concentration of the cumulative desorbed and recovered EO gas (for example, the gas after the first desorption is discharged, the gas after the second to seventh desorption is recovered and reused) detected by gas chromatography reached 1300.8 mg/L, and the recovery rate reached 35.56%. The desorption of the adsorption tower 14 was performed sequentially, and the concentration of EO obtained by the desorption decreased gradually, and the mass of the recovered EO decreased accordingly. By the 15th time of desorption, the concentration of EO obtained by the desorption decreased to about 180.3 mg/L. The mass curve of the cumulative desorption and recovery tended to be flat (as shown in FIG. 11), and the desorption and the recovery were stopped. At this time, the average concentration of the total desorbed and recovered EO gas detected by gas chromatography reached 774.5 mg/L, and the recovery rate reached 65.13%.

Example 2

(1) The fourth gas extractor 22 was used to evacuate the sterilizer 1, creating vacuum pressure in the sterilizer 1 to −0.08 MPa, and pure EO gas was introduced into the sterilizer 1 through the third gas intake pipe 4 until the pressure in the sterilizer 1 reached −0.013 MPa. Then, the sterilizer 1 was filled with nitrogen until the pressure reached 0.05 MPa. The gases in the sterilizer 1 were then mixed uniformly through the third gas extractor 21 and the second circulation pipeline 105 to complete the sterilization and to obtain the sterilization exhaust gas. The sterilization exhaust gas was a mixed gas mainly containing EO and nitrogen. The concentration of EO in the sterilizer 1 detected by the fourth EO detector 31 was 42.23 vol %. At the same time, the gas in the sterilizer 1 was sampled by a sampling device and a gas sampling bag, and the concentration of EO in the sterilization exhaust gas in the sterilizer 1 detected by the gas chromatograph was 756.4 mg/L.

(2) The sterilization exhaust gas in the sterilizer 1 was extracted through the first air gas intake pipe 100 by the fourth gas extractor 22. The flow meter 5 was used to detect and control the flow rate of the sterilization exhaust gas. The sterilization exhaust gas was cooled by the heat exchanger 6. The gas-liquid separator 7 separated water from the cooled sterilization exhaust gas. The separated EO sterilization exhaust gas was dried by the gas dryer 9, and then introduced into the EO adsorption tower 14. The adsorption material in the adsorption tower 14 was 13 × molecular sieve. The cooling and heating system continuously fed cooled water into the water inlet pipe 15 of the adsorption tower 14, which allowed the adsorption tower to be cooled to a temperature ranging from 20° C. to 30° C. After the separated EO sterilization exhaust gas was passed through the plurality of adsorption panels of the EO adsorption tower 14, the residual gas (containing the EO that had not been adsorbed and nitrogen) was discharged through the second pipe 42 and the first gas outtake pipe 16, and the adsorption process was completed. The first EO detector 34 monitored the concentration of EO in the first gas outtake pipe 16 in real-time. At the same time, the gas in the sterilizer 1 was sampled by the sampling device and the gas sampling bag, and the concentration of EO in the discharged gas was detected by the gas chromatograph.

(3) When the adsorbent reached a saturation point, for example, when it was detected that the concentration of EO in the residual gas reached 21 vol %, the flow of EO sterilization exhaust gas into the adsorption tower 14 through the first gas intake pipe 100 was stopped, the feeding of the cooled water into the water intake pipe 15 was stopped, and the desorption was initiated. The cooling and heating system continuously fed 80° C. hot water into the water inlet pipe 15 to heat the adsorption tower 14. The first gas extractor 23 created a vacuum in the gas channel of the adsorption tower 14 to desorb the EO adsorbed by the adsorption material, as previously described, and the desorbed EO evacuated through the second gas outtake pipe 110. The desorbed high-concentration EO gas was stored in the EO gas storage tank 11 by the first compressor 82. When the EO adsorption tower 14 was subject to a vacuum ranging in pressure from −0.065 MPa to −0.086 MPa, the thermal desorption capacity was reduced, and the amount of the gas entering the EO gas storage tank 11 was reduced. At this time, nitrogen gas was introduced into the gas channel through the second gas intake pipe 12 and the second pipe 42 to perform the blow-off process. The desorbed high-concentration EO gas was stored in the EO gas storage tank 11. The gas in the EO gas storage tank 11 was circulated through the second gas extractor 24 and the first circulation pipeline 1105, and the concentration of EO was detected by the second EO detector.

FIG. 11 illustrates the real time concentration of EO in the discharged gas after the EO in the sterilization exhaust gas is absorbed by 13× molecular sieve. The concentration of EO was online-monitored by the EO detector in real time. As shown in FIG. 11, the EO in the adsorption tower 14 was adsorbed by 13× molecular sieve, and the concentration of EO in the discharged residual gas after adsorption was less than 2000 ppm. Thus, the 13× molecular sieve has a very high adsorption efficiency. As the mass of EO introduced into the adsorption tower 14 increases, the concentration of EO in the discharged residual gas gradually increases. FIG. 11 illustrates a phenomenon that the concentration of EO in the discharged residual gas first increases, then decreases, and then increases. There are two main reasons for this phenomenon: a. as the pressure increases, the adsorption efficiency increases and the discharge concentration decreases; b. as the adsorption time increases, the adsorption efficiency increases. The overall trend of the adsorption efficiency of 13× molecular sieve is substantially the same as that of activated carbon. When the adsorption capacity is close to saturation, the adsorption efficiency decreases, and the adsorption amount decreases accordingly, and the concentration of EO in the discharged gas increases rapidly.

The gas chromatography detection indicated that after the sterilization exhaust gas with the concentration of EO of 756.4 mg/L is adsorbed by 13× molecular sieve, the concentration of EO in the discharged residual gas was about 200 ppm, and the adsorption efficiency was above 99.9%. When the concentration of EO in the discharged gas reached 2000 ppm, the adsorption rate (the mass percentage of the absorbed EO and the coconut shell activated carbon) is 14.48%. When the concentration of the discharged EO reaches 21.10 vol %, the adsorption rate reaches 25.05%. The concentration of the desorbed and recovered EO online-monitored by the EO detector ranges from 40 vol % to 95 vol %, the average concentration of the recovered EO detected by the gas chromatography is 1217.3 mg/L, and the recovery rate is 10.20%.

Example 3

(1) The fourth gas extractor 22 was used to create a vacuum in the sterilizer 1 to create a pressure in the sterilizer 1 of −0.086 MPa, and pure EO gas was introduced into the sterilizer 1 through the third gas intake pipe 4 until the pressure in the sterilizer 1 reached −0.013 MPa. Then, nitrogen was introduced into the sterilizer 1 until the pressure reached 0.05 MPa. The gases in the sterilizer 1 were then mixed uniformly through the third gas extractor 21 and the second circulation pipeline 105 to complete the sterilization and to obtain the sterilization exhaust gas. The sterilization exhaust gas was a mixed gas mainly containing EO and nitrogen. The concentration of EO in the sterilizer 1 detected by the fourth EO detector 31 was 45.08 vol %. At the same time, the gas in the sterilizer 1 was sampled by a sampling device and a gas sampling bag, and the concentration of EO in the sterilization exhaust gas in the sterilizer 1 detected by the gas chromatograph was 794.7 mg/L.

(2) The sterilization exhaust gas in the sterilizer 1 was extracted through the first air gas intake pipe 100 by the fourth gas extractor 22. The flow meter 5 was used to detect and control the flow rate. The sterilization exhaust gas was cooled by the heat exchanger 6. The gas-liquid separator 7 separated water from the cooled sterilization exhaust gas. The separated EO sterilization exhaust gas was dried by the gas dryer 9, and then introduced into the gas channel of the EO adsorption tower 14. The adsorption material in the adsorption tower 14 was 4 A molecular sieve. The cooling and heating system continuously fed the cooled water into the water inlet pipe 15 of the adsorption tower 14, which allowed the adsorption tower to be cooled to a temperature ranging from 20° C. to 30° C. After the separated EO sterilization exhaust gas was adsorbed by the EO adsorption tower 14, the residual gas (containing the EO that had not been adsorbed and nitrogen) was discharged through the second pipe 42 and the first gas outtake pipe 16, and the adsorption process was completed. The first EO detector 34 monitored the concentration of EO in the first gas outtake pipe 16 in real-time. At the same time, the gas in the sterilizer 1 was sampled by the sampling device and the gas sampling bag, and the concentration of EO in the discharged sterilization exhaust gas was detected by the gas chromatograph.

(3) When the adsorbent reached the saturation point, for example, when it was detected that the concentration of EO in the residual gas reaches 6 vol %, the flow of EO sterilization exhaust gas into the adsorption tower 14 through the first gas intake pipe 100 was stopped, the feeding of the cooled water into the water intake pipe 15 was stopped, and the desorption process was initiated. The cooling and heating system continuously fed the 80° C. hot water into the water inlet pipe 15 to heat the adsorption tower 14. The first gas extractor 23 created a vacuum in the gas channel of the adsorption tower 14 to desorb the EO adsorbed by the adsorption material, and the desorbed EO evacuated through the second gas outtake pipe 110. The desorbed high-concentration EO gas was stored in the EO gas storage tank 11 by the first compressor 82. When the gas channel of the EO adsorption tower 14 was subject to a vacuum ranging in pressure from −0.065 MPa to −0.086 MPa, the thermal desorption capacity was reduced, and the amount of the gas entering the EO gas storage tank 11 was reduced. At this time, the nitrogen gas was introduced through the second gas intake pipe 12 and the second pipe 42 to perform the blow-off process. The desorbed high-concentration EO gas was stored in the EO gas storage tank 11. The gas in the EO gas storage tank 11 was circulated through the second gas extractor 24 and the first circulation pipeline 1105, and the concentration of EO was detected by the second EO detector.

Analysis of the results: the concentration of EO in the sterilizer 1 was 794.7 mg/L, the gas in the sterilizer 1 was introduced into the adsorption tower 14, and the concentration of EO in the discharged residual gas after the adsorption process by 4 A molecular sieve was 108.2 mg/L, the adsorption rate (the mass percentage of the adsorbed EO and the 4 A molecular sieve) was 10.73%. When the concentration of EO in the discharged residual gas is 250.5 mg/L, the adsorption rate was 11.41%. The average concentration of the desorbed and recovered EO reached 1074.6 mg/L, and the recovery rate was 6.15%.

Table 1 illustrates the performance parameters of adsorption and recovery for the above three embodiments.

TABLE 1

| Serial No. | Adsorption Material | Discharge Conc. | Total Adsorption amount % | Adsorption Efficiency % | Maximum Recovery Conc. vol % | Average Recovery Conc. mg/L | Recovery Rate % |
| --- | --- | --- | --- | --- | --- | --- | --- |
| Ex. 1 | Coconut Shell Activated Carbon | <100 ppm | 10.61 | >99.99 | 99.99 | 1300.8 | 65.13 |
| Ex. 2 | 13X molecular sieve | <2000 ppm | 14.48 | >99.9 | 95.22 | 1217.3 | 10.20 |
| Ex. 3 | 4A molecular sieve | <6 vol % | 10.73 | >99 | 89.34 | 1074.6 | 6.15 |

According to Table 1, the adsorption recovery performance of 4 A molecular sieve is lower than that of coconut shell activated carbon and 13× molecular sieve, and the possible reasons includes: a. differences in properties of different materials; b. differences in intake flow rate and adsorption time.

Comparing coconut shell activated carbon and 13× molecular sieve, the adsorption and recovery performance of 13× molecular sieve is slightly higher than that of coconut shell activated carbon. However, when the same mass of EO is filled, the adsorption efficiency of 13× molecular sieve is slightly lower, and the discharge concentration of 13× molecular is higher than that of coconut shell activated carbon. The desorption capacity of 13× molecular sieve is poor and the recovery rate of 13× molecular sieve is much lower than that of coconut shell activated carbon.

Thus, the EO adsorption tower, EO recovery system, and EO recovery method provided by the above embodiments provide the following technical advantages:

(1) The EO in the EO sterilization exhaust gas is separated, recovered and reused by a low-temperature adsorption and a high-temperature desorption and recovery process. The sterilization exhaust gas is pre-treated for dehumidification, drying and pre-cooling to protect the adsorbent and improve the adsorption and purification capacity of the device. The adsorption tower comprises the water heat exchange system capable of cooling and heating the tower body of the adsorption tower. The water heat exchange system may be configured to cool the tower body during adsorption to promote adsorption, and heat the tower body during desorption and recovery to promote desorption. Nitrogen is used to perform the blow-off process, which enhances the desorption effect and extends a service life of the adsorbent. The adsorption material is placed into an adsorption panel, in which a support frame holds the adsorption material, and the adsorption material is compressed within the support frame. Thus, the adsorption material is fixed in the support frame via a holder. The adsorption panel may be inserted and removed from the gas channel of the tower body, which allows adsorption material in an adsorption panel to be replaced or otherwise maintained. The above embodiments provide that EO is processed by the adsorption process for recycle and reuse, and further that adsorbent used in the adsorption process is processed by a desorption process for reuse. The water used in the water heat exchange system may be collected rainwater, which can also be recycled and reused, and the EO recovery system may be powered by renewable energy, such as a solar power system.

(2) Further embodiments provide that the EO is processed by adsorption for recycle and reuse, and the adsorbent is processed by the desorption process for reuse. Thus, implementations of the above described embodiments are able to save resources and reduce costs, and have the advantages of high performance comparable to higher cost systems, good environmental protection, safety and reliability, reasonable structure, simple operation and good processing efficiency. The concentration of EO in the discharged residual gas is about 10 ppm, the adsorption efficiency is greater than 99.99%, the adsorption rate (the percentage of the absorbed EO and the adsorption material) ranges from 10% to 25%, and the concentration of EO by desorption and recovery ranges from 40 vol % to 99.99 vol %, and the recovery rate ranges from 4% to 65%. Thus, implementation of the above embodiments is beneficial to the popularization and application of EO sterilization, the overall improvement of medical sterilization level, and the realization of a way to process EO sterilization exhaust gas.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. An ethylene oxide adsorption tower, comprising:
   a tower body defining a gas channel extending longitudinally therein, the tower body further comprising a sidewall, wherein the sidewall further comprises a plurality of mounting holes disposed longitudinally along the sidewall and in communication with the gas channel, wherein a bottom portion of the tower body includes a first pipe in communication with the gas channel, and a top portion of the tower body includes a second pipe in communication with the gas channel;
   a plurality of adsorption panels, wherein each of the plurality of adsorption panels is coupled to the tower body through a corresponding respective mounting hole of the plurality of mounting holes, wherein each of the plurality of adsorption panels extends into the gas channel; and
   a sealing door movably coupled to the sidewall of the tower body and configured to selectively fix each of the plurality of adsorption panels to a respective mounting hole of the plurality of mounting holes, wherein the sealing door comprises a door plate and sealing strip, wherein the sealing strip is arranged between the door plate and the tower body to create an outline corresponding to each of the plurality of adsorption panels to create a seal with the tower body and around each of the plurality of adsorption panels.

2. The ethylene oxide adsorption tower of claim 1, wherein the plurality of adsorption panels comprises a first adsorption panel, wherein the first adsorption panel comprises:
- a support frame comprising a plurality of first ventilation holes, the support frame configured to be inserted into a respective first mounting hole of the plurality of mounting holes;
- an adsorption material disposed within the support frame;
- a holder coupled to the support frame and configured to fix the adsorption material in the support frame, the holder comprising a plurality of second ventilation holes.

3. The ethylene oxide adsorption tower of claim 2, wherein the plurality of first ventilation holes are disposed on a bottom plate of the support frame, and the holder is a cover plate covering a top opening of the support frame.

4. The ethylene oxide adsorption tower of claim 2, wherein diameters of the first and second ventilation holes are less than a particle size of the adsorption material.

5. The ethylene oxide adsorption tower of claim 1, further comprising a gas distributor disposed in the gas channel and located below the plurality of adsorption panels, wherein the gas distributor further comprises a plurality of third ventilation holes in communication with the first pipe and the gas channel.

6. The ethylene oxide adsorption tower of claim 5, wherein the plurality of third ventilation holes are disposed on a top plate of the gas distributor.

7. The ethylene oxide adsorption tower of claim 1, further comprising a water heat exchange system provided on the tower body and configured to cool or heat the tower body.

8. The ethylene oxide adsorption tower of claim 1, wherein each of the plurality of adsorption panels is individually configured to be replaceable as a whole.

9. An ethylene oxide recovery system, comprising:
- an ethylene oxide adsorption tower comprising:
  - a tower body defining a gas channel extending longitudinally therein, the tower body further comprising a sidewall, wherein the sidewall further comprises a plurality of mounting holes disposed longitudinally along the sidewall and in communication with the gas channel, wherein a bottom portion of the tower body includes a first pipe in communication with the gas channel, and a top portion of the tower body includes a second pipe in communication with the gas channel;
  - a plurality of adsorption panels, wherein each of the plurality of adsorption panels is coupled to the tower body through a corresponding respective mounting hole of the plurality of mounting holes, wherein each of the plurality of adsorption panels extends into the gas channel; and
  - a sealing door movably coupled to the sidewall of the tower body and configured to selectively fix each of the plurality of adsorption panels to a respective mounting hole of the plurality of mounting holes, wherein the sealing door comprises a door plate and sealing strip, wherein the sealing strip is arranged between the door plate and the tower body to create an outline corresponding to each of the plurality of adsorption panels to create a seal with the tower body and around each of the plurality of adsorption panels;
- a first gas intake pipe coupled to the first pipe and configured to introduce a gas containing ethylene oxide into the gas channel via the first pipe;
- a first gas outtake pipe coupled to the second pipe and configured to output the gas after it has passed through the plurality of adsorption panels and is discharged from the second pipe;
- a second gas outtake pipe coupled to the first pipe; and
- a recovery assembly coupled to the second gas outtake pipe, the recovery assembly configured to extract desorbed gas from the gas channel through the second gas outtake pipe and the first pipe, wherein the desorbed gas includes ethylene oxide desorbed from the adsorption material.

10. The ethylene oxide recovery system of claim 9, wherein the recovery assembly comprises a first gas extractor and a gas storage tank, the first gas extractor is located upstream of the gas storage tank, and a first ethylene oxide detector is coupled to the first gas outtake pipe.

11. The ethylene oxide recovery system of claim 9, wherein a first circulation pipeline is connected between a gas inlet and a gas outlet of the gas storage tank, a second gas extractor and a second ethylene oxide detector are coupled to the first circulation pipeline.

12. The ethylene oxide recovery system of claim 9, further comprising a third gas outtake pipe coupled to the second gas outtake pipe, wherein a connecting position of the third gas outtake pipe and the second gas outtake pipe is located between the first gas extractor and the gas storage tank.

13. The ethylene oxide recovery system of claim 11, wherein a third ethylene oxide detector is coupled to the third gas outtake pipe.

14. The ethylene oxide recovery system of claim 11, wherein a filter is coupled to the second gas outtake pipe and is located upstream of the first gas extractor, a first compressor is further coupled to the second gas outtake pipe and is located downstream of the first gas extractor.

15. The ethylene oxide recovery system of claim 9, further comprising a second gas intake pipe coupled to the second pipe and configured to introduce a desorption gas into the gas channel through the second pipe, wherein the desorption gas is configured to aid desorption of the adsorption material via a blow off process.

16. The ethylene oxide recovery system of claim 9, further comprising:
- a sterilizer coupled to the first gas intake pipe; and
- a third gas intake pipe coupled to the sterilizer and configured to introduce an ethylene oxide sterilization gas into the sterilizer, wherein the gas containing ethylene oxide generated in the sterilizer is discharged through the first gas intake pipe.

17. The ethylene oxide recovery system of the claim 16, further comprising a second circulation pipeline, a third gas extractor, and a fourth ethylene oxide detector, wherein the second circulation pipeline is coupled to a gas inlet and a gas outlet of the sterilizer, respectively, and the third gas extractor and the fourth ethylene oxide detector are coupled to the second circulation pipeline.

18. The ethylene oxide recovery system of the claim 16, wherein a flow meter, a heat exchanger, a gas-liquid separator, a fourth gas extractor, a second compressor, and a gas dryer are sequentially mounted in the first gas intake pipe in an airflow direction.

19. A method for recovering ethylene oxide, comprising:
- obtaining, from a sterilizer, a sterilization exhaust gas;
- discharging the sterilization exhaust gas into a first gas intake pipe coupled to an ethylene oxide adsorption tower, the ethylene oxide adsorption tower comprising:
  - a tower body defining a gas channel extending longitudinally therein, the tower body further comprising a sidewall, wherein the sidewall further comprises a plurality of mounting holes disposed longitudinally along the sidewall and in communication with the gas channel, wherein a bottom portion of the tower body includes a first pipe in communication with the gas channel, and a top portion of the tower body includes a second pipe in communication with the gas channel;

a plurality of adsorption panels, wherein each of the plurality of adsorption panels is coupled to the tower body through a corresponding respective mounting hole of the plurality of mounting holes, wherein each of the plurality of adsorption panels extends into the gas channel; and a sealing door movably coupled to the sidewall of the tower body and configured to selectively fix each of the plurality of adsorption panels to a respective mounting hole of the plurality of mounting holes, wherein the sealing door comprises a door plate and sealing strip, wherein the sealing strip is arranged between the door plate and the tower body to create an outline corresponding to each of the plurality of adsorption panels to create a seal with the tower body and around each of the plurality of adsorption panels;

introducing the sterilization exhaust gas into the gas channel;

passing, via a gas distributor of the ethylene oxide adsorption tower, the sterilization exhaust gas through the plurality of adsorption panels sequentially from bottom to top in the gas channel;

cooling the ethylene oxide adsorption tower while the sterilization exhaust gas is passed through the plurality of adsorption panels sequentially from bottom to top in the gas channel, by continuously feeding cool water, which is at a temperature ranging from 20° C. to 30° C., into a water inlet pipe of the ethylene oxide adsorption tower;

adsorbing, via adsorption materials in the plurality of adsorption panels, ethylene oxide in the sterilization exhaust gas;

discharging, via the second pipe, a residual gas, wherein the residual gas comprises the sterilization exhaust gas after it has passed through the plurality of adsorption panels;

detecting a concentration of the ethylene oxide in the residual gas;

stopping flow of the sterilization exhaust gas into the first pipe when the concentration of ethylene oxide exceeds a preset value;

extracting desorbed gas in the gas channel through the first pipe, wherein desorbed gas includes ethylene oxide desorbed from the adsorption material; and storing the ethylene oxide in the desorbed gas in a gas storage tank.

20. The method of claim 19, further comprising:
heating the ethylene oxide adsorption tower while desorbed gas in the gas channel is extracted.

21. The method of claim 19, wherein a concentration of the ethylene oxide in the sterilization exhaust gas ranges from 1 vol % to 99.99 vol %.

* * * * *